United States Patent
Peng et al.

(10) Patent No.: US 9,758,822 B2
(45) Date of Patent: *Sep. 12, 2017

(54) GRAPHENE TRANSISTOR GATED BY CHARGES THROUGH A NANOPORE FOR BIO-MOLECULAR SENSING AND DNA SEQUENCING

(71) Applicant: International Business Machines Corporation, Armonk, NY (US)

(72) Inventors: Hongbo Peng, Chappaqua, NY (US); Gustavo A. Stolovitzky, Riverdale, NY (US); Wenjuan Zhu, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/163,141

(22) Filed: Jan. 24, 2014

(65) Prior Publication Data

US 2014/0141521 A1    May 22, 2014

Related U.S. Application Data

(60) Division of application No. 13/477,099, filed on May 22, 2012, which is a continuation of application No. 13/448,509, filed on Apr. 17, 2012.

(51) Int. Cl.
*G01N 27/62* (2006.01)
*C12Q 1/68* (2006.01)
(Continued)

(52) U.S. Cl.
CPC ..... *C12Q 1/6869* (2013.01); *G01N 33/48721* (2013.01); *B82Y 5/00* (2013.01); *Y10T 436/143333* (2015.01)

(58) Field of Classification Search
CPC ........... C12Q 1/6869; C12Q 2565/631; G01N 33/48721; G01N 27/3275; B82Y 5/00
(Continued)

(56) References Cited

U.S. PATENT DOCUMENTS 6,627,067 B1 *  9/2003  Branton ............... B24B 37/013
                                                    204/403.06
7,001,792 B2    2/2006  Sauer et al.
(Continued)

FOREIGN PATENT DOCUMENTS

CN    102169105 A    8/2011
EP      1037366 A2   9/2000
(Continued)

OTHER PUBLICATIONS

Luan, Binquan, Ali Afzali, Stefan Harrer, Hongbo Peng, Philip Waggoner, Stas Polonsky, Gustavo Stolovitzky, and Glenn Martyna. "Tribological Effects on DNA Translocation in a Nanochannel Coated with a Self-Assembled Monolayer." Journal of Physical Chemistry B 114 (2010): 17172-7176.*
(Continued)

*Primary Examiner* — Keith Hendricks
*Assistant Examiner* — Kourtney S Carlson
(74) *Attorney, Agent, or Firm* — Cantor Colburn LLP; Vazken Alexanian

(57) ABSTRACT

A technique for a nanodevice is provided. A reservoir is separated into two parts by a membrane. A nanopore is formed through the membrane, and the nanopore connects the two parts of the reservoir. The nanopore and the two parts of the reservoir are filled with ionic buffer. The membrane includes a graphene layer and insulating layers. The graphene layer is wired to first and second metal pads to form a graphene transistor in which transistor current
(Continued)

flowing through the graphene transistor is modulated by charges or dipoles passing through the nanopore.

6 Claims, 10 Drawing Sheets

(51) Int. Cl.
G01N 33/487 (2006.01)
B82Y 5/00 (2011.01)

(58) Field of Classification Search
USPC .......................... 324/71.1, 464; 257/29, 253
See application file for complete search history.

(56) References Cited

U.S. PATENT DOCUMENTS

| | | | |
|---|---|---|---|
| 7,846,738 B2* | 12/2010 | Golovchenko et al. | ........ 436/86 |
| 2007/0020146 A1* | 1/2007 | Young | .............. G01N 33/48721 422/82.01 |
| 2007/0190542 A1 | 8/2007 | Ling et al. | |
| 2008/0157354 A1 | 7/2008 | Zhang et al. | |
| 2008/0185295 A1 | 8/2008 | Briman et al. | |
| 2010/0066348 A1 | 3/2010 | Merz et al. | |
| 2010/0327847 A1* | 12/2010 | Leiber et al. | ................. 324/71.1 |
| 2011/0217763 A1 | 9/2011 | Rasooly et al. | |
| 2011/0236984 A1 | 9/2011 | Sun et al. | |
| 2011/0279125 A1 | 11/2011 | Bedell et al. | |
| 2012/0037919 A1 | 2/2012 | Xu et al. | |
| 2012/0146162 A1 | 6/2012 | Cho et al. | |
| 2014/0190833 A1* | 7/2014 | Lieber | .................... B82Y 30/00 204/627 |
| 2015/0160159 A1 | 6/2015 | Afzali-Ardakani et al. | |

FOREIGN PATENT DOCUMENTS

| | | | |
|---|---|---|---|
| EP | 2424092 A1 | 2/2012 | |
| WO | WO0181896 A1 | 11/2001 | |
| WO | WO2009020682 A2 | 2/2009 | |
| WO | WO2011082419 A2 | 7/2011 | |
| WO | 2012138357 A1 | 10/2012 | |
| WO | WO2013016486 A1 | 1/2013 | |

OTHER PUBLICATIONS

R. Akeson M., Branton D., Kasianowicz J. J., Brandin E., and Deamer D. W., "Microsecond Timescale Discrimination Among Polycytidylic Acid, Polyadenylic Acid, and Polyuridylic Acid as Homopolymers or as Segments within Single RNA Molecules," Biophys. J. 77 3227-33 (1999).
Y. He, et al., "Bilayer Graphene Lateral Contacts for DNA Sequencing," arXiv preprint arXiv: 1206.4199, 2012, 16 pages.
C. Palego, et al., "Nanopore Test Circuit for Single-Strand DNA Sequencing," 12th Topical Meeting on Silicon Monolithic Integrated Circuits in RF Systems (SiRF), 2012, pp. 101-104.
B. Venkatesan, et al., "Stacked Graphene-Al2O3 Nanopore Sensors for Sensitive Detection of DNA and DNA-Protein Complexes," ACS Nano, vol. 6, No. 1, 2011, pp. 441-450.
Bae, S. et al., "Roll-to-Roll Production of 30-Inch Graphene Films for Transparent Electrodes," Nature Nanotechnology 5 574 (2010); pp. 574-578.
A. Bergvall et al., "Graphene Nanogap for Gate-Tunable Quantum-Coherent Single-Molecule Electronics," Phys. Rev. B., vol. 84, No. 15, 2011, 155451, 7 pages.
Branton D., et al., The Potential and Challenges of Nanopore Sequencing, Nature Biotechnology 26(10) 1146-1153 (2008).

A. K. Geim and K. S. Novoselov, "The Rise of Graphene," Nature Materials 6 183 (2007); pp. 183-191.
Gracheva M. E., Xiong A., Aksimentiev A., Schulten K., Timp G. and Leburton J. P., "Simulation of the Electric Response of DNA Translocation Through a Semiconductor Nanopore-Capacitor," Nanotechnology 17 622-633 (2006).
H. Im et al., "A Dielectric-Modulated Field-Effect Transistor for Biosensing," Published online: Jun. 24, 2007, Nature Nanotechnology, vol. 2, Jul. 2007, pp. 430-434.
J. Hass, W.A. de Heer and E.H. Conrad, "The Growth and Morphology of Epitaxial Multilayer Graphene," Journal of Physics: Condensed Matter. 20, 323202 (2008); 28 pages.
Heng J. B., Ho C., Kim T., Timp R., Aksimentiev A., Grinkova Y. V., Sligar S., Schulten K. and Timp G., "Sizing DNA Using a Nanometer-Diameter Pore," Biophys. J. 87 2905-91 (2004).
Kasianowicz J. J., Brandin E., Branton D. and Deamer D. W., "Characterization of Individual Polynucleotide Molecules Using a Membrane Channel," Proc. Natl Acad. Sci. USA 93 13770-773 (1996).
K. S. Kim, et al. "Large-Scale Pattern Growth of Graphene Films for Stretchable Transparent Electrodes," Nature 457, 706-710 (2009).
Lagerqvist J., Zwolak M. and Di Ventra M., "Fast DNA Sequencing via Transverse Electronic Transport," Nano Lett. 6 779-782 (2006).
Meller A., Nivon L., Brandin E., Golovchenko J. and Branton D., "Rapid Nanopore Discrimination Between Single Polynucleotide Molecules," Proc. Natl Acad. Sci. USA 97 1079-84 (2000).
D. Farmer, et al., "Vertical Stacking of Graphene in a Field-Effect Transistor," U.S. Appl. No. 13/683,148, filed Nov. 21, 2012.
H. Peng, et al., "Graphene Transistor Gated by Charges Through a Nanopore ofr Bio-Molecule Sensing and DNA Sequencing," U.S. Appl. No. 13/448,509, filed Apr. 17, 2012.
Fernando Patolsky, Gengfeng Zheng, Oliver Hayden, Melike Lakadamyali, Xiaowei Zhuang, and Charles M. Lieber, "Electrical detection of single viruses," Departments of Chemistry and Chemical Biology and Physics and Division of Engineering and Applied Sciences, Harvard University, Cambridge, MA 02138, Contributed by Charles M. Lieber, Aug. 20, 2004, pp. 1-6.
H. W. C. Postma, "Rapid Sequencing of Individual DNA Molecules in Graphene Nanogaps," Nano Lett., vol. 10, No. 2, Publication Date (Web): Jan. 4, 2010, pp. 420-425.
J. Prasongkit et al., "Transverse Conductance of DNA Nucleotides in a Graphene Nanogap from First Principles," arXiv:1012.1669v2 [physics.ins-det], [v1] Dec. 8, 2010, [v2] Jan. 14, 2011, Nano Lett., vol. 11, No. 5, 2011, pp. 1941-1945.
Soni G., and Meller A., "Progress Towards Ultrafast DNA Sequencing Using Solid State Nanopores," Clin. Chem. 3 1996-01 (2007); 6 pages.
Eric Stern, James F. Klemic, David A. Routenberg, Pauline N. Wyrembak, Daniel B. Turner-Evans, Andrew D. Hamilton, David A. Lavan, Tarek M. Fahmy and Mark A. Reed, "Label-free immunodetection with CMOS-compatible semiconducting nanowires," Nature Publishing Group, vol. 445, Feb. 2007, doi:10.1038/nature05498, pp. 1-4.
Storm A. J., Chen J. H., Ling X. S., Zandbergen H. W., and Dekker C., "Fabrication of Solid-State Nanopores with Single-Nanometre Precision," Nature Materials 2, 537-540 (2003).
S. Vassanelli, P. Fromherz, "Transistor Probes Local Potassium Conductances in the Adhesion Region of Cultured Rat Hippocampal Neurons," The Journal of Neuroscience, Aug. 15, 1999, 19(16):6767-6773, Department of Membrane and Neurophysics, Max-Planck-Institute for Biochemistry.
Liu, S., "Boron Nitride Nanopores: Highly Sensitive DNA Single-Molecule Detectors," Advanced Materials, 2013, 25, pp. 4549-4554.

* cited by examiner

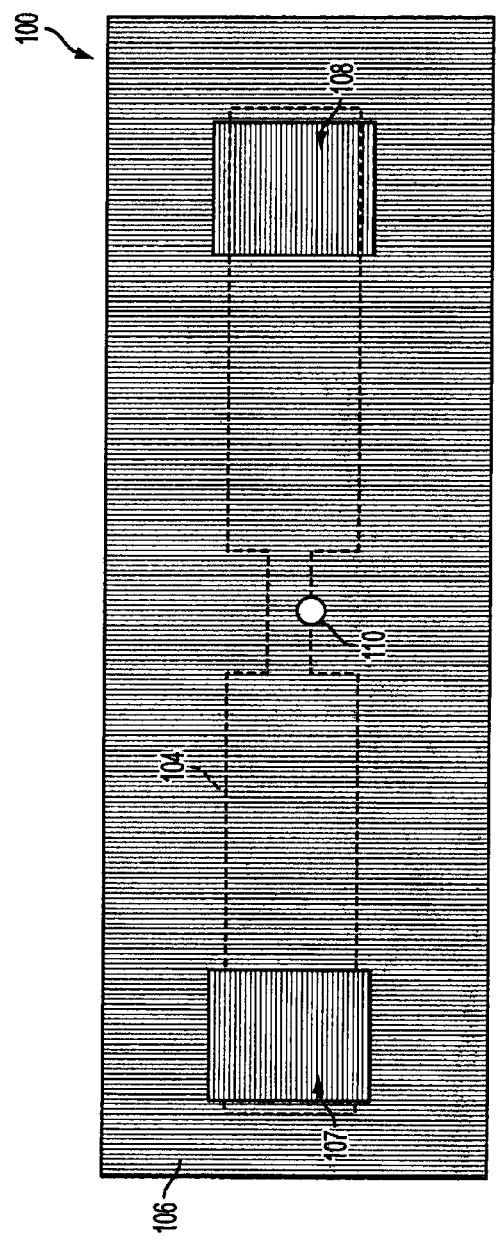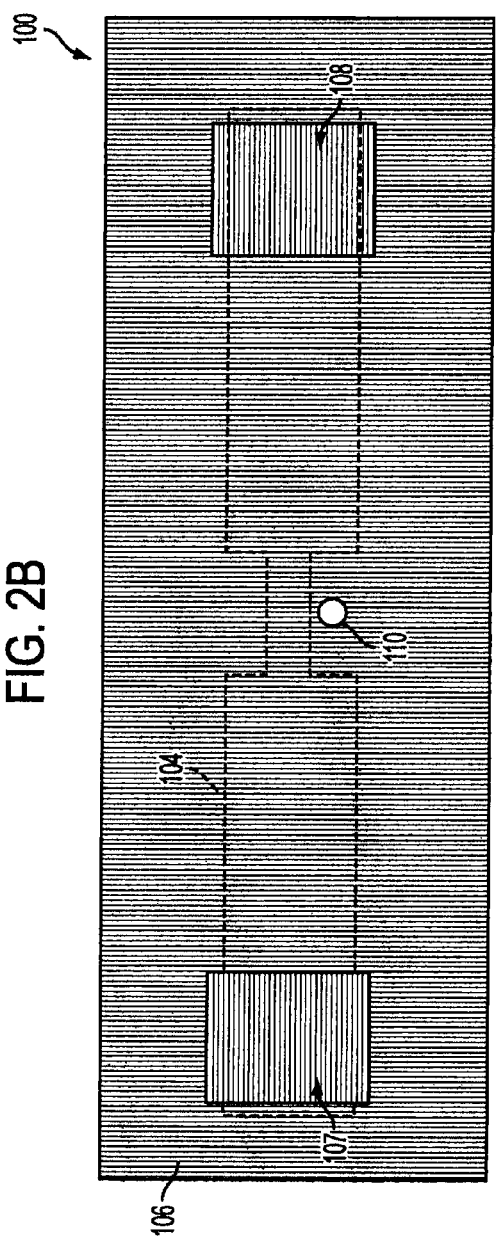

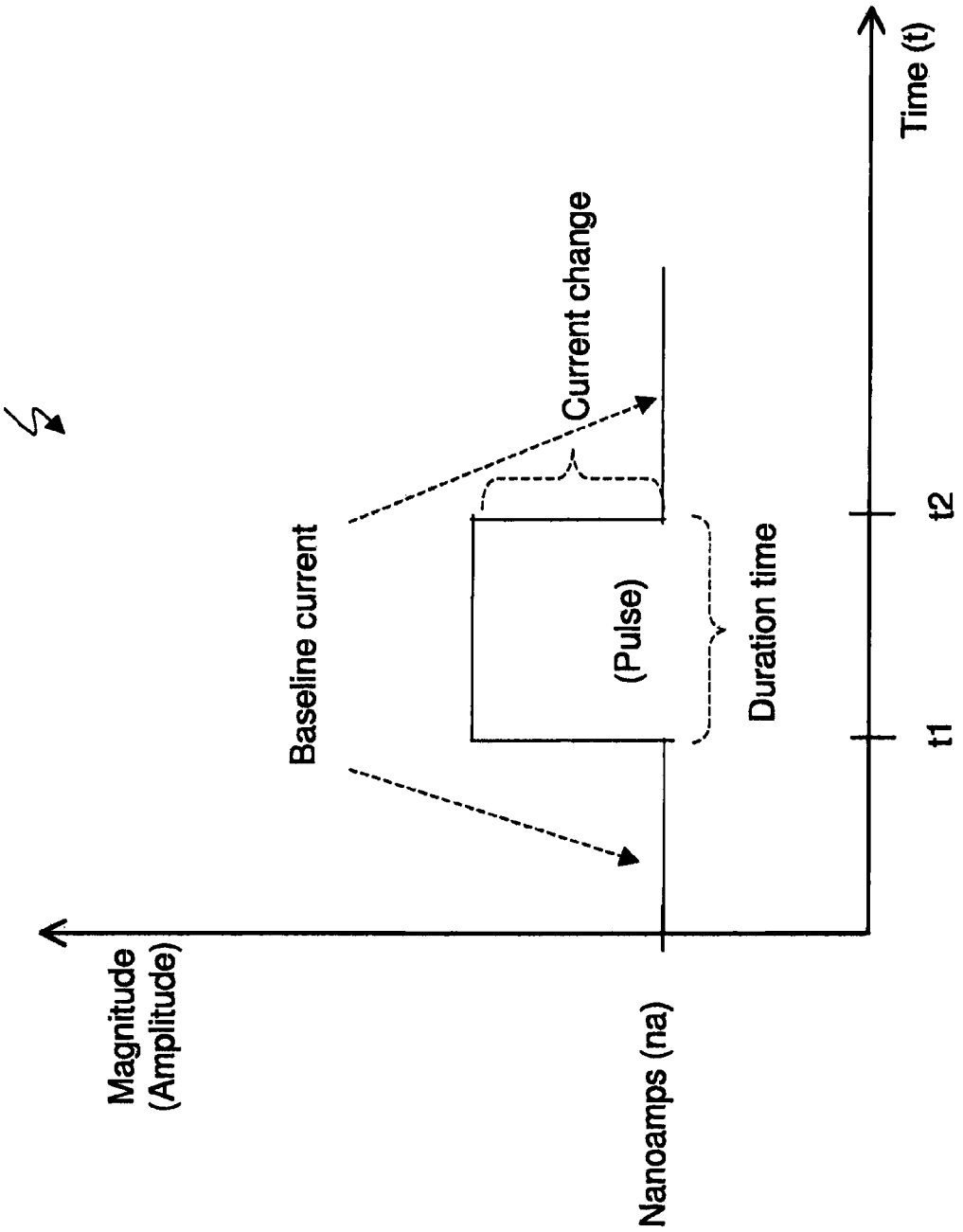

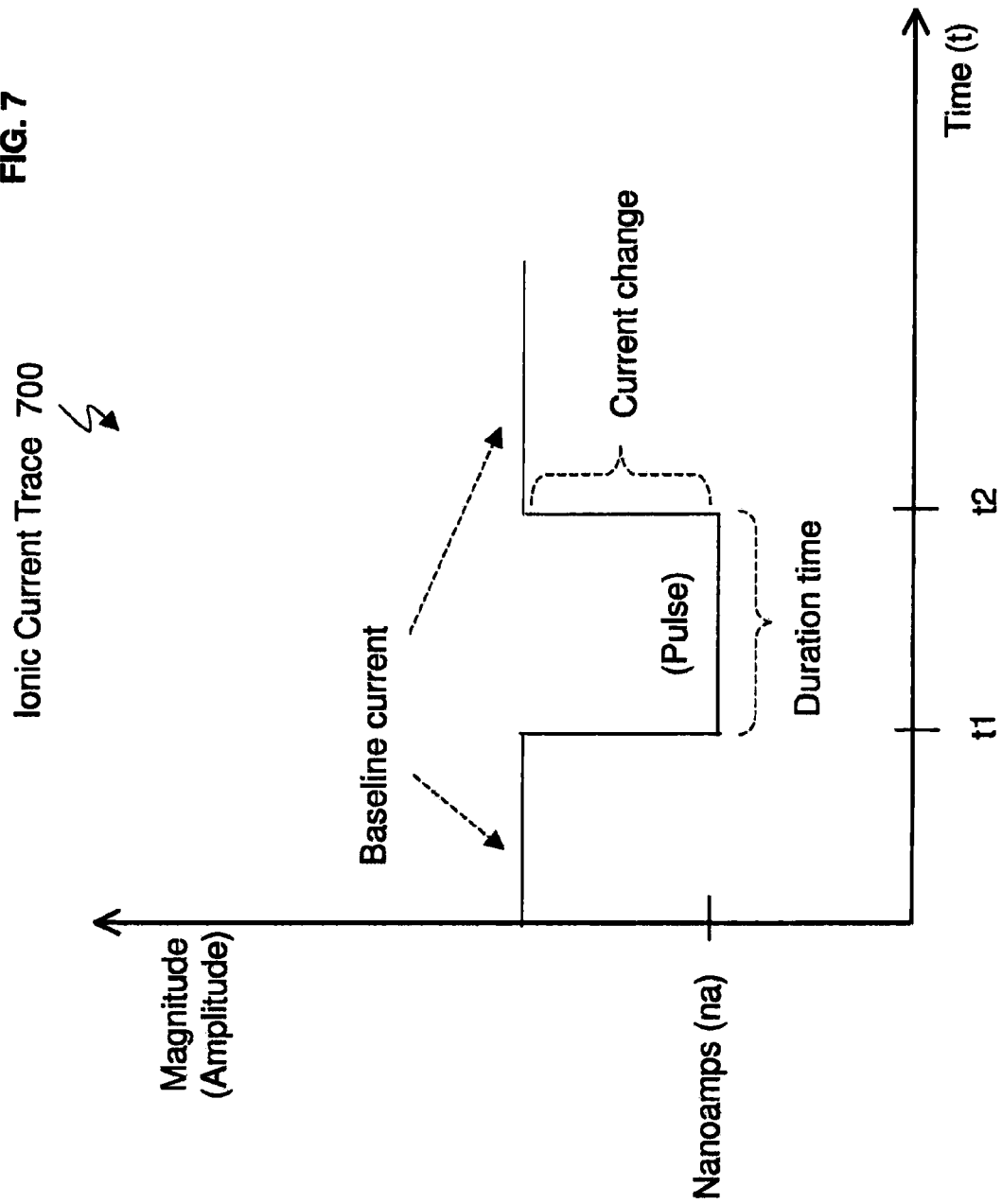

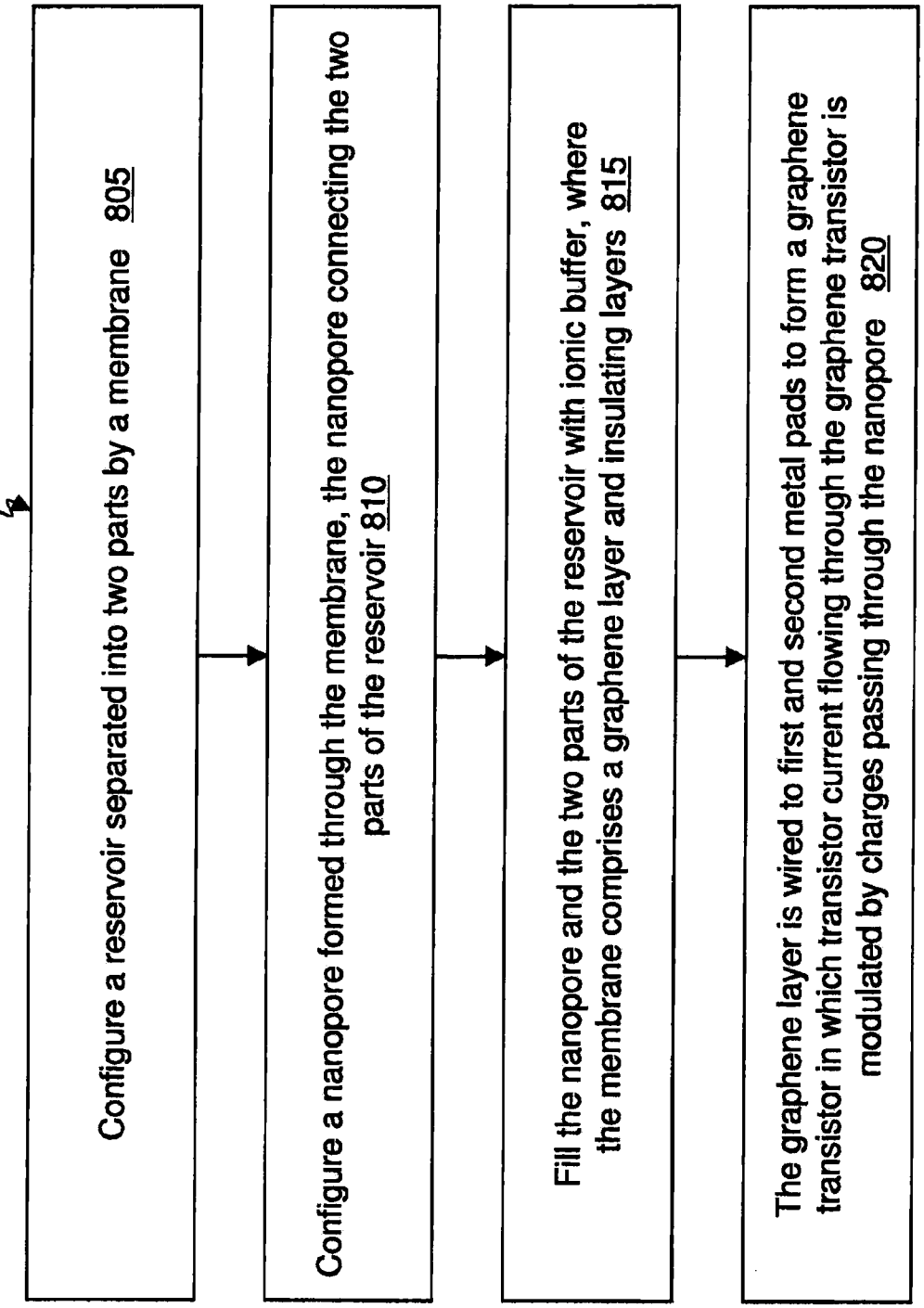

FIG. 9 900

Configure a reservoir separated into two parts by a membrane 905

→ Configure a nanopore formed through the membrane, the nanopore connecting the two parts of the reservoir 910

→ Fill the nanopore and the two parts of the reservoir with ionic buffer, where the membrane comprises a graphene layer and insulating layers 915

→ The graphene layer is wired to first and second metal pads to form a graphene transistor in which transistor current flowing through the graphene transistor is modulated by charges passing through the nanopore, where the charges correspond to at least one of a base and a biomolecule 920

→ The nanopore is coated with an organic layer configured to at least one of interact with the base differently than other bases and interact with the biomolecule differently than other biomolecules 925

GRAPHENE TRANSISTOR GATED BY CHARGES THROUGH A NANOPORE FOR BIO-MOLECULAR SENSING AND DNA SEQUENCING

This is a divisional application that claims the benefit of U.S. patent application Ser. No. 13/477,099 filed May 22, 2012, which is a continuation of U.S. patent application Ser. No. 13/448,509 filed Apr. 17, 2012, the contents of which are incorporated in entirety by reference herein.

BACKGROUND

The present invention relates generally to identifying and differentiating molecules, and more specifically, to identifying and differentiating molecules using a graphene nanopore transistor.

Nanopore sequencing is a method for determining the order in which nucleotides occur on a strand of deoxyribonucleic acid (DNA). A nanopore (also referred to as a pore, nanochannel, hole, etc.) can be a small hole in the order of several nanometers in internal diameter. The theory behind nanopore sequencing is about what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods. For example, an electric field might attract the DNA towards the nanopore, and it might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome. Two issues in nanopore DNA sequencing are controlling the translocation of DNA through the nanopore and differencing individual DNA bases.

SUMMARY

According to an embodiment, a method for electrically differentiating DNA nucleobases and/or identifying biomolecules is provided. The method includes configuring a reservoir separated into two parts by a membrane, and configuring a nanopore formed through the membrane. The nanopore connects the two parts of the reservoir. The method includes filling the nanopore and the two parts of the reservoir with ionic buffer. The membrane includes a graphene layer and insulating layers. The graphene layer is wired to first and second metal pads to form a graphene transistor in which transistor current flowing through the graphene transistor is modulated by charges and/or dipoles passing through the nanopore.

According to an embodiment, a method for electrically differentiating DNA nucleobases and/or identifying biomolecules. The method includes configuring a reservoir separated into two parts by a membrane, and configuring a nanopore formed through the membrane. The nanopore connects the two parts of the reservoir. The method also includes filling the nanopore and the two parts of the reservoir with ionic buffer. The membrane includes a graphene layer and insulating layers. The graphene layer is wired to first and second metal pads to form a graphene transistor in which transistor current flowing through the graphene transistor is modulated by charges and/or dipoles passing through the nanopore. The charges and/or dipoles correspond to at least one of a nucleobase and a biomolecule. The nanopore is coated with an organic layer configured to at least one of interact with the nucleobase differently than other nucleobases and/or interact with the biomolecule differently than other biomolecules.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 2B shows a top view of the graphene nanopore transistor device, illustrating the geometry of the buried graphene layer according to an embodiment.

FIG. 2C shows a top view of the graphene nanopore transistor device, illustrating the geometry of the buried graphene layer according to an embodiment.

FIG. 6 illustrates a graph of a transistor current pulse according to an embodiment.

FIG. 7 illustrates a graph of an ionic current pulse according to an embodiment.

FIG. 8 is a flow chart illustrating a method for differentiating and identifying bases and biomolecules in a nanopore according to an embodiment.

FIG. 9 is a flow chart illustrating a method for differentiating and identifying bases and biomolecules in a nanopore according to an embodiment.

DETAILED DESCRIPTION

Field effect transistor sensors have been demonstrated for sensing biomolecules, and are especially suitable for reducing the required amount of reagents by leveraging their high sensitivity. However, single molecule accuracy and high spatial resolution of, e.g., 0.7 nm (nanometers) for DNA sequencing has not yet been demonstrated using this approach.

Embodiments propose the use of a graphene transistor on a freestanding membrane with a nanopore passing through it. Single molecules can be driven through the nanopore one by one, and as they go through, each individual molecule can modulate the current through the graphene transistor. This configuration allows molecular detection with single molecule accuracy. As the graphene layer can be as thin as 0.335 nm (nanometers), the spatial resolution of this approach can be 0.335 nm, which is enough for DNA sequencing purpose.

Figure 1:
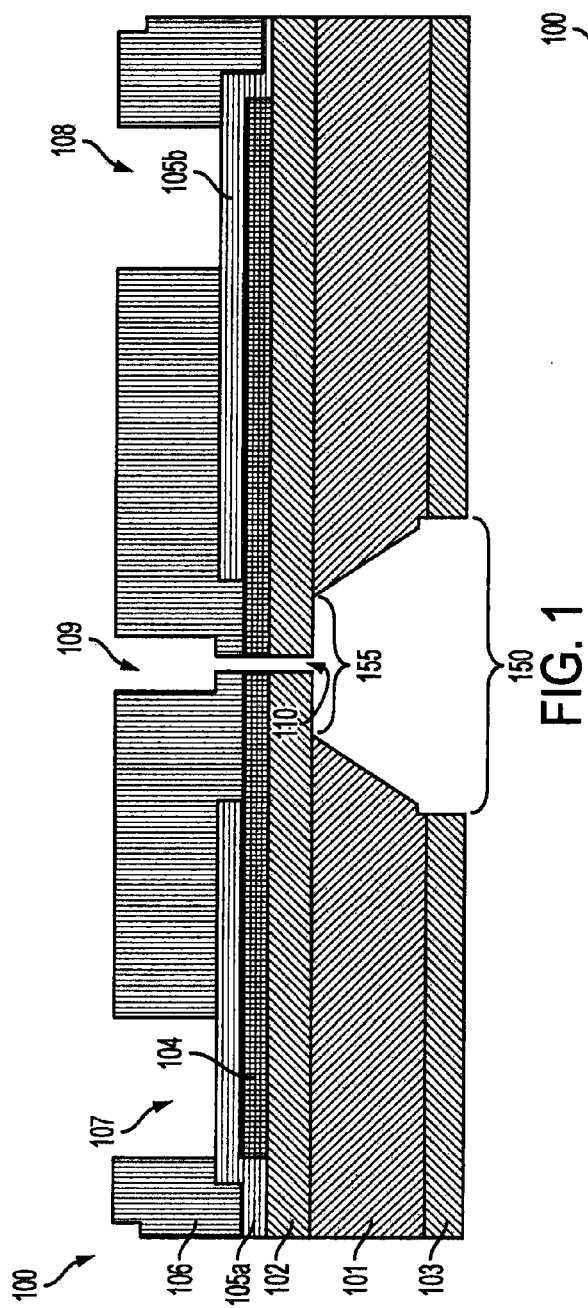
FIG. 1 illustrates a fabrication process of a cross-section graphene nanopore transistor device according to an embodiment.

FIG. 1 illustrates a fabrication process of a cross-section nanopore graphene transistor device 100, with detailed material layers and process flow (figure not to scale) according to an embodiment. The graphene nanopore transistor device 100 is a chip.

The graphene nanopore transistor device 100 includes a substrate 101 which may be a silicon (Si) substrate. A layer 102 is an insulation layer which may be LPCVD (low pressure chemical vapor deposition) $Si_3N_4$ (around 30 nm in thickness). A layer 103 is an insulation layer which may be 250 nm thick $Si_3N_4$, including 30 nm LPCVD $Si_3N_4$ and 220 nm PECVD (plasma enhanced chemical vapor deposition) $Si_3N_4$.

To form the graphene layer 104, thin films of graphene can be formed by CVD (chemical vapor deposition) growth on metal, by exfoliation of bulk graphite, or by epitaxial grown on SiC (silicon carbide) by high temperature decomposition of its surface and sublimation of Si. Among these methods, graphene grown on copper can produce the largest film area (up to 30 inches in width). The underlying copper can be etched away by copper etchant and transferred to targeting substrate by using thermal release tape, PMMA (polymethyl methacrylate), or PDMS (polydimethylsiloxane). In this application, the graphene film/layer 104 can be transferred onto LPCVD $Si_3N_4$ layer 102 and be patterned through photolithography or ebeam lithography followed by reactive ion etching (RIE) based on $O_2$ plasma. The photo/e-beam resist can be cleaned by Acetone without damaging the graphene layer 104. The reason to pattern the graphene layer 104 is to make it smaller than the following metal/electrically conductive pads 105a and 105b, which can be deposited by ebeam evaporation with patterned photoresist on top and can be patterned by a metal lifting off process. The metal pads 105a and 105b can be a stack of Ti/Pd/Au (titanium/palladium/gold). As the metal pads 105a and 105b partially covers the top of both the graphene layer 104 and the substrate 101, this (covering) will fix (prevent) the graphene layer 104 from slipping during any following process. Insulation (passivation) layer 106 (made of thin $Si_3N_4$ (around 30 nm), 200 nm $SiO_2$, and 200 nm Si3N4) is deposited on top of the metal pads 105a and 105b.

A window area 150 is opened on layer 103 through photolithography and RIE, after which KOH (potassium hydroxide) or TMAH (tetramethylammonium hydroxide) can be used to etch through the Si substrate 101 at the window area 150, to make a free-standing membrane 155 on the front side.

Figure 3:
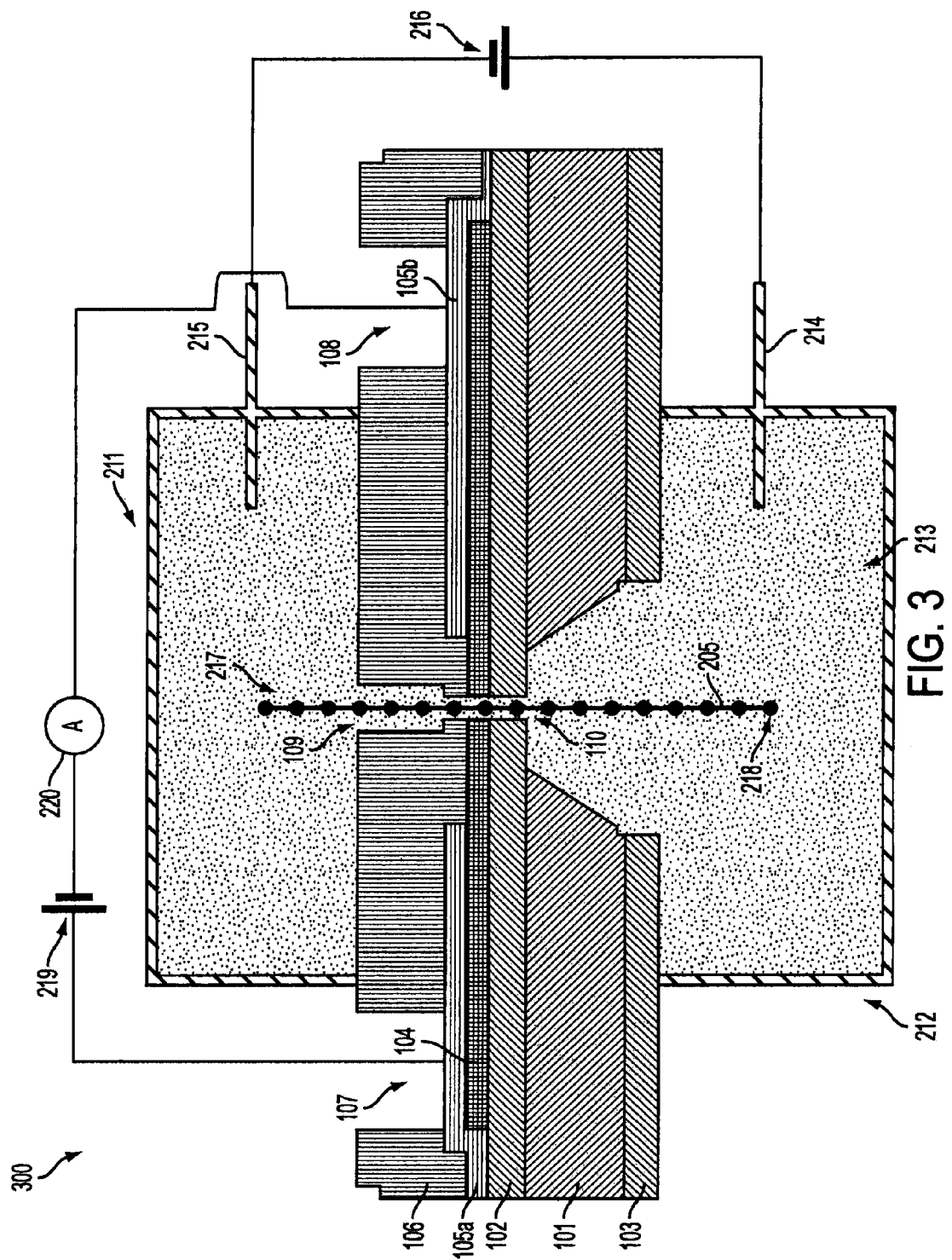
FIG. 3 is a setup of the graphene nanopore transistor device for DNA and/or RNA sequencing according to an embodiment.
Figure 4:
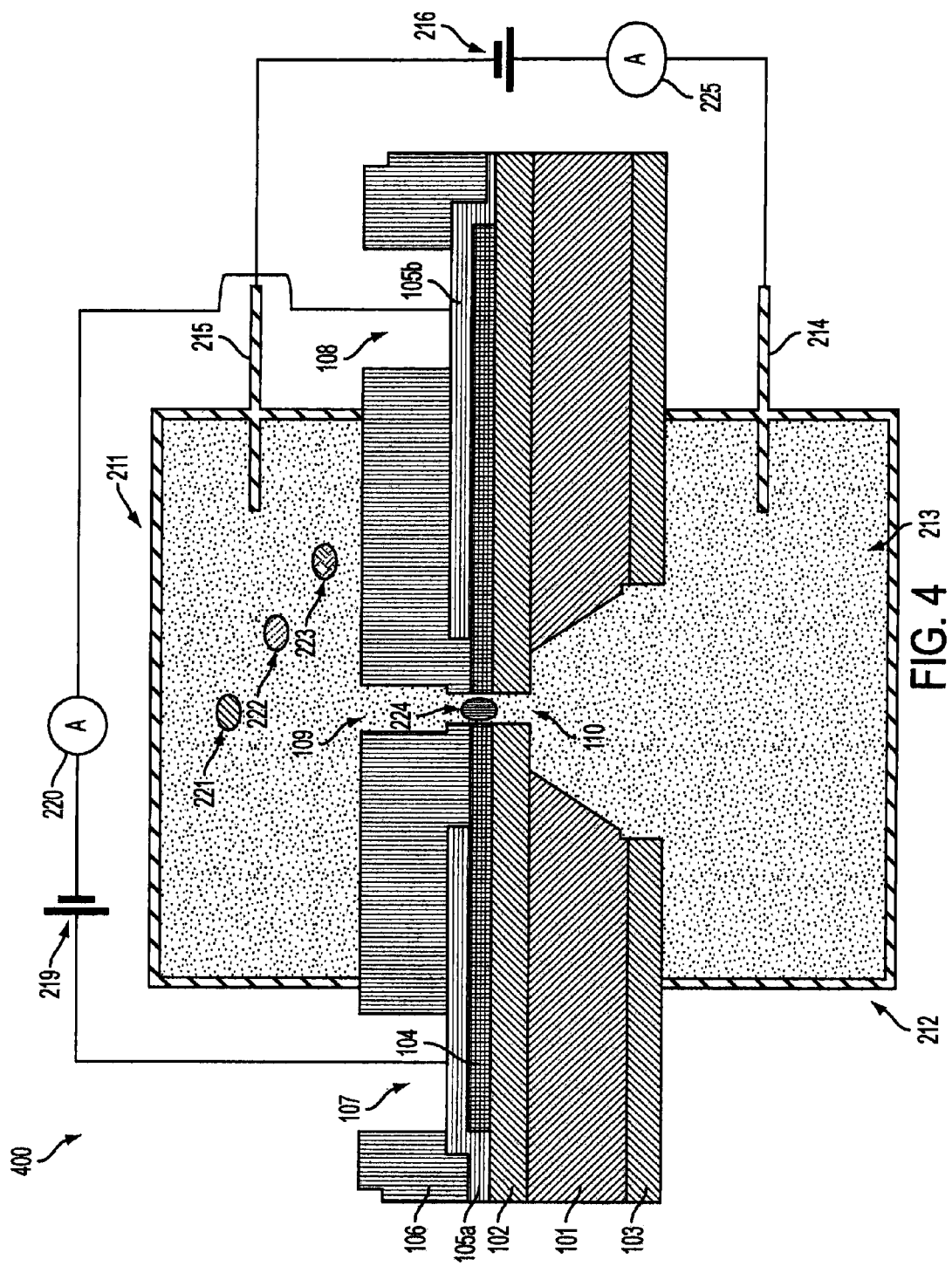
FIG. 4 is a setup of the graphene nanopore transistor device for biomolecule sensing according to an embodiment.
Figure 5:
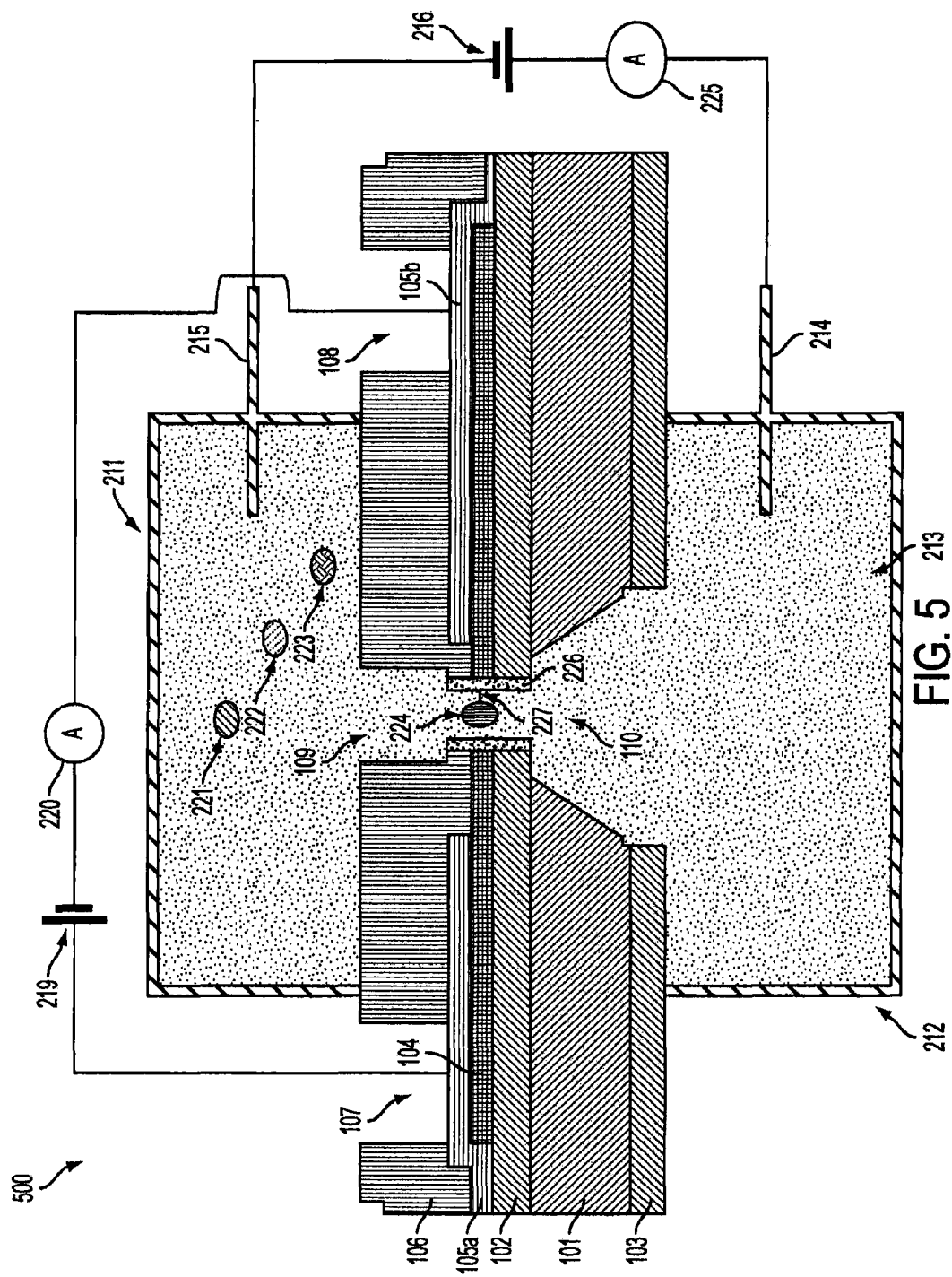
FIG. 5 shows a setup of the graphene nanopore transistor device for biomolecule sensing according to an embodiment.

Vias (holes) 107 and 108 are etched through insulation layer 106. The etching stops on the metal pads 105a and 105b to provide access to the metal pads 105a and 105b via external electrical probes (which include wires as shown in FIGS. 3, 4, and 5). Via (hole) 109 is partially etched through insulation layer 106 (etching the 200 nm $SiO_2$ and 200 nm $Si_3N_4$ layers (of layer 106) and then stopping on 30 nm thick $Si_3N_4$ layer (of layer 106), which is employed to protect the graphene layer 104 underneath). Nanopore 110 through the stacked layers 106, 104, and 102 with sizes ranging from 0.5 nm to 100 nm can be made via TEM (transmission electron microscopy) drilling or other techniques.

Figure 2A:
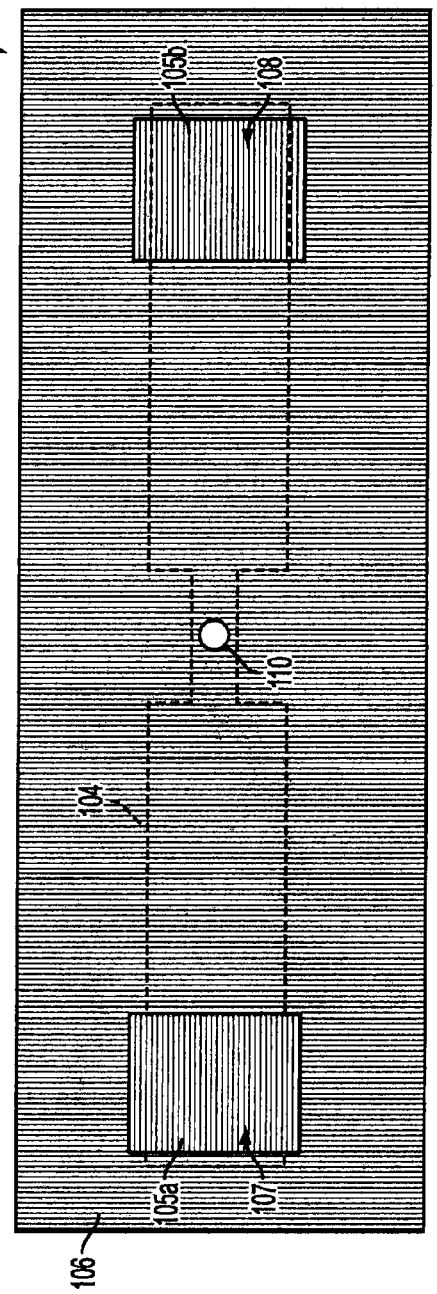
FIG. 2A shows a top view of the graphene nanopore transistor device, illustrating the geometry of the buried graphene layer according to an embodiment.

FIG. 2A shows an implementation of the top view of the graphene nanopore transistor device 100, illustrating the geometry of the buried graphene layer 104. The graphene layer 104 has a narrow part (neck) around the location where the nanopore 110 is made so that charges on biomolecules and/or nucleobases will largely affect the transistor current through the graphene nanopore transistor device 100. The nanopore 110 is shown at the center of the narrowest part of the graphene layer 104. The nanopore 110 can also be offset and/or even out of the edge of the graphene layer 104, as illustrated in FIG. 2B and FIG. 2C.

FIG. 2B show another implementation of the top view of the graphene nanopore transistor device 100, illustrating the geometry of the buried graphene layer 104 in which the nanopore 110 is offset on only part of the graphene layer 104. The circumference of the nanopore 110 is not completely through the graphene layer 104, while the circumference of the nanopore 110 fully continues through layers 106 and 102.

FIG. 2C shows another implementation of the top view of the graphene nanopore transistor device 100, illustrating the geometry of the buried graphene layer 104 in which the nanopore 110 is off the edge of the graphene layer 104 without touching the graphene layer 104. The circumference of the nanopore 110 is not (at all) through the graphene layer 104 (but is proximate or nearly adjacent to the graphene layer 104 with distance of about a couple nanometers to a couple of micrometers), while the circumference of the nanopore 110 fully continues through layers 106 and 102.

FIG. 3 shows a setup 300 of the graphene nanopore transistor device 100 for DNA (or RNA) sequencing according to an exemplary embodiment. FIG. 3 shows a cross-sectional view of the graphene nanopore transistor device 100. Elements 101-110 in FIG. 3 are the same as described FIG. 1, and elements 150 and 155 are not repeated in FIG. 3 so as not to overly complicate FIG. 3. Top reservoir 211 and bottom reservoir 212 (which could be any orientation including one side and another side) are sealed to each side of the (chip) graphene nanopore transistor device 100.

Reservoirs 211 and 212, and the nanopore 110 are then filled with ionic buffer 213. The ionic buffer 213 is an electrical conducting fluid of ions. A single strand DNA molecule 217 (with bases 218 illustrated as ovals and the backbone 205 illustrated as a solid line) is loaded into the nanopore 110 by an electrical voltage bias of a voltage source 216, applied across the nanopore 110 via two electrochemical electrodes 214 and 215, which were dipped in the ionic buffer 213 of the two reservoirs 212 and 211.

The DNA molecule 217 has charges on its molecular backbone 205 as well as different dipole moments for each of its DNA bases 218. When DNA molecule 217 is in ionic buffer, the free mobile ions in the ionic buffer 213 will concentrate around the charged DNA molecule 217 to electrically screen any charge on the DNA. The ions that screen the charged DNA are called counter-ions. As the counter ions are under thermal agitation, so the charged ions will spread out with a length scale, called Debye length, instead of tightly wrapping the DNA molecule 217. When the ionic concentration of ionic buffer 213 is low enough that the Debye length is comparable to or larger than the radius of nanopore 110, and the electrical field from both the charge on the backbone 205 and dipole moment on bases 218 will be largely unscreened from counter-ions and be interacting with the graphene layer 104.

Dipole moment ($\mu$) is the measure of net molecular polarity, which is the magnitude of the charge Q at either end of the molecular dipole times the distance r between the charges, which is shown by the equation $\mu = Q \times r$. Dipole moments tell us about the charge separation in a molecule. The larger the difference in electronegativities of bonded atoms, the larger the dipole moment.

Voltage (DC or AC) by voltage source 219 is applied on the two ends of the graphene layer 104 via two the metal pads 105a and 105b at holes 107 and 108 respectively, and current measured by ammeter 220 will be modulated by the charges (of each base 218) passing through the nanopore 110. In this way, different DNA bases 218 (with different dipole moments) will be able to modulate transistor current measured by the ammeter 220 and can be differentiated based on the transistor current signal measured by ammeter 220 for respective bases 218 that pass through the nanopore 110 at the graphene layer 104. Since the graphene layer 104 can be as thin as 0.335 nm (smaller than base pair distance 0.7 nm (which is the distance from one base 218 to the next base 218) of a stretched single strand DNA), this approach has enough spatial resolution to detect individual bases 218.

The baseline transistor current can be measured by the ammeter 220 when no base 218 is present in the nanopore 110. For example, the transistor current flow (measured by the ammeter 220) travels from the voltage source 219, through the metal pad 105a via hole 107, through one side of the graphene layer 104 then directly to the other side (via the free-standing membrane 155) of the graphene layer 104, and out through the metal pad 105b via the hole 108 to be measured by ammeter 220 (note that as seen in FIGS. 2A-2C, the graphene layer 104 is continuous from one side to the other side except there is hole (nanopore 110) which does not completely cut/sever the graphene layer 104 into two parts).

The base 218 can be identified/sequenced by the characteristics of the transistor current pulse triggered due to the presence of the base 218 inside the nanopore 110, such as, for example, the magnitude and the time duration of the transistor current pulse (the time it takes the DNA base to pass through the nanopore) as expected for the given base 218. When the base 218 is present inside the nanopore 110, the presence of this particular base 218 causes the transistor current to modulate (i.e., change). The transistor current flow (e.g., measured by the ammeter 220 when the base 218 is inside the nanopore 110) travels from the voltage source 219, through the metal layer 105a via hole 107, through one side of the graphene layer 104 to be modulated by the base 218 in the nanopore 110, to the other side (via the free-standing membrane 155) of the graphene layer 104, and out the metal layer 105b via the hole 108. FIG. 6 illustrates a graph 600 of the transistor current pulse measured by ammeter 220 (which can be graphed via a software application 1060 in FIG. 10) as discussed herein according to an embodiment. This is just one example that may be displayed on the display (input/output device 1070) of a computer 1000 via the software application 1060. The graph 600 shows the magnitude/amplitude (e.g., in nanoamps) of the transistor current pulse height (relative to the baseline level of transistor current when there is no DNA (base 218) and/or molecules (e.g., biomolecule 221, 222, 223, 224 in FIGS. 4 and 5) inside the nanopore 110) on the y-axis and shows the time duration (t) of the transistor current pulse on the x-axis. For each respective biomolecule 221, 222, 223, 224 and/or each respective base 218, a corresponding transistor current trace (of its transistor current pulse measured when inside the nanopore 110) is graphed with a time duration (t) and magnitude as seen in FIG. 6. For example, the base 218 (and/or biomolecule 221-224) in the nanopore 110) modulates/changes the baseline transistor current (which is measured when no base/molecule is in the nanopore 110) by the example current change amount (for the time duration) shown in graph 600. When present in the nanopore 110, this modulation/change (including the shape and other characteristics of the transistor current pulse) in transistor current (measured by the ammeter 220) is used by the software application 1060 to determine the type of base 218 from the other bases 218 of the DNA module 217 and/or to determine the type of biomolecule from the other biomolecules.

FIG. 4 shows a setup 400 of the graphene nanopore transistor device 100 for biomolecule sensing according to an embodiment. FIG. 4 shows a cross-sectional view of the graphene nanopore transistor device 100. The elements in FIG. 4 are the same as described FIGS. 1 and 3. In FIG. 4, however, biomolecules 221-224, such as protein, DNA, RNA, etc., have been loaded into the graphene nanopore transistor device 100. When the biomolecules 221-224 are individually driven through the nanopore 110 via either fluidic pressure bias between the two sides (of the two reservoirs 211 and 212) of the graphene nanopore transistor device 100 (chip) (when the biomolecules 221-224 are uncharged), voltage bias applied by voltage source 216 (when the biomolecules 221-224 are charged) or both, at least two parameters can be extracted: (1) ionic current as measured by ammeter 225, depending on the size of the molecule/biomolecule in the nanopore 110; and (2) modulation of the graphene transistor current measured by the ammeter 220, which depends on the total surface charge of the biomolecule 221-224 in the nanopore 110 (as discussed in FIG. 6). As one embodiment for data analysis, by (the software application 1060 on the computer 1000) plotting these two parameters in a scatter plot, one (the software application 1060) will be able to differentiate and identify each type of the biomolecules 221-224. As discussed above in FIG. 6, each respective biomolecule 221-224 in the nanopore 110 (one at a time) modulates the baseline current (which is measured when no base/biomolecule is in the nanopore 110) by the current change amount as shown in graph 600. This modulation (change) in transistor current (measured by the ammeter 220) is used by the software application 1060 to determine the type of biomolecule (e.g., biomolecule 224 presently in the nanopore 110) from the other biomolecules 221, 222, 223 in the reservoir 211.

Additionally, the ionic current (measured by ammeter 225 for the baseline ionic current when no base/molecule is in the nanopore 110) flows from electrochemical electrode 215 to the conductive ionic buffer 213 in the upper chamber (i.e., top reservoir 211), then to the nanopore 110, then to the ionic buffer 213 in the bottom chamber (i.e., bottom reservoir 212), and then to electrochemical electrode 214.

When a biomolecule (such as biomolecule 221, 222, 223, and/or 224) is in the nanopore 110, the biomolecule affects (modulates) the (baseline) ionic current. The ionic current (measured by ammeter 225 when a base 218 and/or biomolecule 221-224 is individually in the nanopore 110) flows from electrochemical electrode 215 to the conductive ionic buffer 213 in the upper chamber (i.e., top reservoir 211), then to the nanopore 110 where, e.g., the biomolecule 224 changes the flow of ionic current, then to the ionic buffer 213 in the bottom chamber (i.e., bottom reservoir 212), and then to electrochemical electrode 214.

The ionic current (when voltage is applied by voltage source 216) as measured by ammeter 225 is modulated depending on the size of the molecule/biomolecule in the nanopore 110 as shown in FIG. 7, where a larger size changes to ionic current more than a smaller size molecule/biomolecule. The graph 700 shows the magnitude/amplitude (e.g., in nanoamps) of the ionic current pulse height (relative to the baseline level when there is no DNA (base 218) and/or molecules (e.g., biomolecule 221, 222, 223, 224) inside the nanopore) on the y-axis and shows the time duration (t) of the ionic current pulse on the x-axis. For each respective biomolecule 221, 222, 223, 224 (and/or each respective base 218), a corresponding ionic current trace (of its ionic current pulse measured when inside the nanopore 110) is graphed with a time duration (t) and magnitude as seen in FIG. 7. For example, the individual biomolecule 221-224 (and/or base 218) in the nanopore 110 modulates the baseline current (which is measured when no base/molecule is in the nanopore 110) by the example current change amount shown in graph 700. This modulation (change) in ionic current (measured by the ammeter 225) is used by the software application 1060 to determine the type of biomolecule from the other biomolecules 221-224 (and/or determine the type of base 218 from the other bases 218 of the DNA module 217).

Accordingly, a biomolecule can be identified/sequenced by the magnitude of its ionic current pulse due to its presence inside the nanopore and the time duration of its ionic current pulse (the time it takes the DNA base to pass through the nanopore) as expected for a given biomolecule of the same type.

FIG. 5 shows a setup 500 of the graphene nanopore transistor device 100 for biomolecule sensing according to an embodiment. FIG. 5 shows a cross-sectional view of the graphene nanopore transistor device 100. The elements in FIG. 5 are the same as described in FIGS. 1, 3, and 4. In FIG. 5, however, the setup 500 shows that the nanopore 110 can also be coated with an organic coating/layer 226, which can differentially interact with each type of biomolecules 221-224 (and/or base 218), e.g., forming transient chemical bonds 227, etc. In this way, a third parameter (in addition to the first and second parameters) can be extracted, and the third parameter is the time (i.e., duration time) it takes for the molecule 221-224 to pass through the nanopore 110, which can be measured from the pulse time duration of the current signal from (either) the ionic current measured by ammeter 225 and/or transistor current measured by ammeter 220.

Further regarding the organic coating 226, the organic coating 226 is applied to the nanopore 110 on the insulation layer 106, the graphene layer 104, and the insulation layer 102. The organic coating 226 has one end bonded to the inner surface of (layers 106, 104, 102 inside) the nanopore 110 and the other end (functional group) is free in the nanopore 110 to interact with biomolecules 221-224 and/or DNA bases 218 of a molecule. The other free end (functional group) of the organic coating 226 forms transient bonds to the bases of molecules and/or to biomolecules as discussed herein. The transient bonds 227 of the organic coating 226 keep the biomolecules and/or DNA molecule from moving while in the nanopore 110. A voltage bias (by the voltage source 216) can be applied to break the transient bonds and then move the biomolecules and/or DNA molecule through the nanopore 110 as desired.

Further, information regarding the organic coating can be found in application Ser. No. 13/359,743, filed Jan. 27, 2012, entitled "DNA MOTION CONTROL BASED ON NANOPORE WITH ORGANIC COATING FORMING TRANSIENT BONDING TO DNA" and application Ser. No. 13/359,729, filed Jan. 27, 2012, entitled "ELECTRON BEAM SCULPTING OF TUNNELING JUNCTION FOR NANOPORE DNA SEQUENCING" which are herein incorporated by reference in their entirety.

The strength of the transient bonds 227 to each respective biomolecule 221, 222, 223, 224 is different based on the type of biomolecule that is presently in the nanopore 110. As such, the time duration (plot of time versus magnitude as seen in graph 700 on, e.g., a display of the computer 1000 operatively connected to the ammeter 225 and/or voltage source 216 as understood by one skilled in the art) of the measured ionic current (by ammeter 225) will be longer in time for the biomolecule (e.g., biomolecule 224) having a stronger transient bond 227 to the organic coating 226. The time duration in the nanopore 110 is based on the combination of the transient bond 227 plus the respective charge of the particular biomolecule 221, 222, 223, 224. As such, for the same transient bond 227, a biomolecule with less charge stays in the nanopore 110 for a longer time duration than a biomolecule with more charge, thus requiring a larger amount of voltage to drive the less-charged biomolecule out of the nanopore 110.

There are many choices for the organic coating 226, and the organic coating 226 can be chosen to have a special interaction (i.e., a strong transient bond) to certain types of biomolecules which will increase the time duration of the ionic current for that particular biomolecule, and increase the detection of that particular biomolecule. Examples pairs of the biomolecule and organic coating 226 that form a strong bond include but are not limited to an antigen (biomolecule) and an antibody (organic coating) pair, DNA base (biomolecules) and its complementary DNA base (organic coating) pair, hydrophobic molecules and hydrophobic coating pairs, hydrophilic molecules and hydrophilic coating pair, etc.

DNA base A bonds with T while base C bonds with G. In other words, Base A and T are complementary bases for each other, while base C and G are complementary bases for each other.

In chemical-physics, hydrophobicity is the physical property of a molecule (known as a hydrophobe) that is repelled from a mass of water. Hydrophobic molecules tend to be non-polar and, thus, prefer other neutral molecules and non-polar solvents. Hydrophobic molecules in water often cluster together, forming micelles. Examples of hydrophobic molecules include the alkanes, oils, fats, and greasy substances in general. Hydrophobic materials are used for oil removal from water, the management of oil spills, and chemical separation processes to remove non-polar from polar compounds. On the other side, a hydrophile is a molecule or other molecular entity that is attracted to, and tends to be dissolved by, water. A hydrophilic molecule or portion of a molecule is one that has a tendency to interact with or be dissolved by water and other polar substances. Hydrophilic substances can seem to attract water out of the air, the way salts (which are hydrophilic) do. Sugar, too, is hydrophilic, and like salt is sometimes used to draw water out of foods. There are hydrophilic and hydrophobic parts of the cell membrane. A hydrophilic molecule or portion of a molecule is one that is typically charge-polarized and capable of hydrogen bonding, enabling it to dissolve more readily in water than in oil or other hydrophobic solvents. Hydrophilic and hydrophobic molecules are also known as polar molecules and nonpolar molecules, respectively. Some hydrophilic substances do not dissolve. This type of mixture is called a colloid. Soap, which is amphipathic, has a hydrophilic head and a hydrophobic tail, allowing it to dissolve in both waters and oils.

FIG. 8 is a flow chart of a method 800 for electrically differentiating bases 218 of the DNA molecule 217 and/or identifying biomolecules 221-224 according to an embodiment.

At block 805, a reservoir (top and bottom reservoirs 211 and 212) is separated into two parts by a membrane (e.g., layers 102, 104, 106). A nanopore 110 is formed through the membrane, and the nanopore 110 connects the two parts of the reservoir at block 810. The nanopore 110 and the two parts of the reservoir are filled with ionic buffer 213 at block 815. The membrane comprises a graphene layer 104 and insulating layers 102 and 106. At block 820, the graphene layer 104 is wired to first and second metal pads (e.g., metal pads 105a and 105b via holes 107 and 108 respectively) to form a graphene nanopore transistor 100 in which transistor current flowing through the graphene nanopore transistor 100 is modulated by charges (of the base 218 and/or biomolecules 221-224 respectively) passing through the nanopore 110.

The charges correspond to a base 218 of the molecule 217. When the base 218 is in the nanopore 110, the transistor current modulates based on the charges or dipole moment of the base 218 to form a transistor current pulse (e.g., as shown in FIG. 6). The base 218 is determined/differentiated (i.e., sequenced) based on a magnitude, a time duration, and/or a shape of the transistor current pulse when the particular base 218 is in the nanopore 110.

The charges correspond to a biomolecule (such as biomolecules 221-224). When the particular biomolecule (e.g., biomolecule 224) is in the nanopore 110, the transistor current modulates based on the charges or dipole of that particular biomolecule 224 to form a transistor current pulse (e.g., as shown in FIG. 6). The particular biomolecule 224 is determined/differentiated based on a magnitude and a time duration of the transistor current pulse when the biomolecule 224 is in the nanopore 110.

When a voltage (by voltage source 216) is applied across the nanopore 110, an ionic current is changed based on a size of the biomolecule (e.g., biomolecule 224) to form an ionic current pulse, and the biomolecule 224 is determined based on a magnitude and a time duration of the ionic current pulse when the biomolecule is in the nanopore 110 (e.g., as shown in FIG. 7).

FIG. 9 is a flow chart of a method 900 for electrically differentiating bases 218 of the DNA molecule 217 and/or identifying biomolecules 221-224 according to an embodiment.

At block 905, a reservoir (top and bottom reservoirs 211 and 212) is separated into two parts by a membrane (e.g., layers 102, 105, 106). A nanopore 110 is formed through the membrane, and the nanopore 110 connects the two parts of the reservoir at block 910. The nanopore 110 and the two parts of the reservoir are filled with ionic buffer 213 at block 915. The membrane comprises a graphene layer 104 and insulating layers 102 and 106.

The graphene layer 104 is wired to first and second metal pads (e.g., metal pads 105a and 105b via holes 107 and 108 respectively) to form a graphene nanopore transistor 100 in which transistor current flowing through the graphene nanopore transistor 100 is modulated by charges passing through the nanopore 110, where the charges correspond to at least one of a base 218 and/or a biomolecule 221-224 at block 920. To distinguish an individual base 218 and/or an individual biomolecule (e.g., biomolecule 224), the nanopore 110 is coated with an organic coating/layer 226 configured to at least one of interact with the particular type of base 218 differently (e.g., form a stronger bond) than other types of bases 218 and/or interact with the particular biomolecule (e.g., biomolecule 224) differently (e.g., form a stronger bond) than other biomolecules 221-223 at block 925.

When the charges or dipoles correspond to the base 218 of a molecule 217 and when the base 218 is in the nanopore 110, the transistor current modulates based on the charges or dipoles of the base 218 to form a transistor current pulse (e.g., shown in FIG. 6). As such, the base 218 is determined based on a magnitude, a time duration, and/or a shape of the transistor current pulse when the base 218 is in the nanopore 110.

When the charges or dipoles correspond to the biomolecule (e.g., biomolecule 224) and when the biomolecule is in the nanopore 110, the transistor current modulates based on the charges or dipoles of the biomolecule to form a transistor current pulse (e.g., as shown in FIG. 6). As such, the biomolecule is determined based on a magnitude and a time duration of the transistor current pulse when the biomolecule is in the nanopore 110.

When a voltage is applied (by the voltage source 216) across the nanopore 110, an ionic current is changed based on a size of the biomolecule 221-224 to form an ionic current pulse (e.g., as shown in FIG. 7). As such, the biomolecule is determined/differentiated based on a magnitude and a time duration of the ionic current pulse when the biomolecule (e.g., biomolecule 224) is in the nanopore 110.

When the molecule 217 is a DNA molecule, the bases 218 respectively comprise at least one of adenine, guanine, thymine, and cytosine. When the molecule 217 is an RNA molecule, the bases 218 respectively comprise at least one of adenine, cytosine, guanine, uracil, thymine, pseudouridine, methylated cytosine, and guanine.

Figure 10:
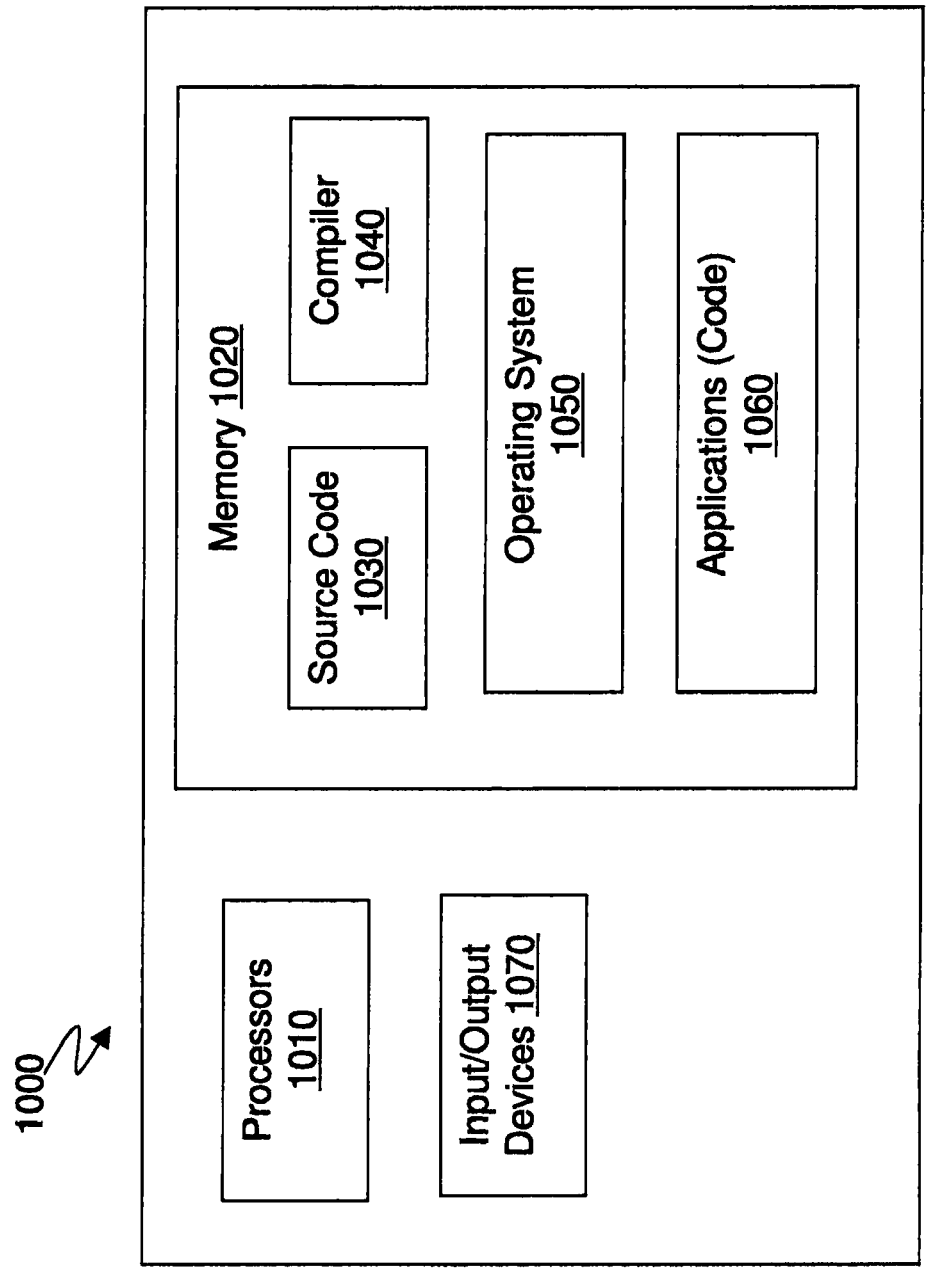
FIG. 10 illustrates an example of a computer having capabilities, which may be included in and/or combined with embodiments.

FIG. 10 illustrates an example of a computer 1000 (e.g., as part of the computer setup for testing and analysis) having capabilities, which may be included in exemplary embodiments. Various methods, procedures, modules, flow diagrams, tools, applications, circuits, elements, and techniques discussed herein may also incorporate and/or utilize the capabilities of the computer 1000. Moreover, capabilities of the computer 1000 may be utilized to implement features of exemplary embodiments discussed herein. One or more of the capabilities of the computer 1000 may be utilized to implement, to connect to, and/or to support any element discussed herein (as understood by one skilled in the art) in FIGS. 1-9. For example, the computer 1000 which may be any type of computing device and/or test equipment (including ammeters, voltage sources, connectors, etc.). Input/output device 1070 (having proper software and hardware) of computer 1000 may include and/or be coupled to the nanodevices discussed herein via cables, plugs, wires, electrodes, etc. Also, the communication interface of the input/output devices 1070 comprises hardware and software for communicating with, operatively connecting to, reading, and/or controlling voltage sources, ammeters, and ionic current traces (e.g., magnitude and time duration of ionic current and or transistor current), etc., as discussed herein. The user interfaces of the input/output device 1070 may include, e.g., a track ball, mouse, pointing device, keyboard, touch screen, etc., for interacting with the computer 1000, such as inputting information, making selections, independently controlling different voltages sources, and/or displaying, viewing and recording ionic current traces for each base, molecule, biomolecules, etc.

Generally, in terms of hardware architecture, the computer 1000 may include one or more processors 1010, computer readable storage memory 1020, and one or more input and/or output (I/O) devices 1070 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 1010 is a hardware device for executing software that can be stored in the memory 1020. The processor 1010 can be virtually any custom made or commercially available processor, a central processing unit (CPU), a data signal processor (DSP), or an auxiliary processor among several processors associated with the computer 1000, and the processor 1010 may be a semiconductor based microprocessor (in the form of a microchip) or a macroprocessor.

The computer readable memory 1020 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 1020 may incorporate electronic, magnetic, optical, and/or other types of storage media. Note that the memory 1020 can have a distributed architecture, where various components are situated remote from one another, but can be accessed by the processor 1010.

The software in the computer readable memory 1020 may include one or more separate programs, each of which comprises an ordered listing of executable instructions for implementing logical functions. The software in the memory 1020 includes a suitable operating system (O/S) 1050, compiler 1040, source code 1030, and one or more applications 1060 of the exemplary embodiments. As illustrated, the application 1060 comprises numerous functional components for implementing the features, processes, methods, functions, and operations of the exemplary embodiments. The application 1060 of the computer 1000 may represent numerous applications, agents, software components, modules, interfaces, controllers, etc., as discussed herein but the application 1060 is not meant to be a limitation.

The operating system 1050 may control the execution of other computer programs, and provides scheduling, input-output control, file and data management, memory management, and communication control and related services.

The application 1060 may be a source program, executable program (object code), script, or any other entity comprising a set of instructions to be performed. When a source program, then the program is usually translated via a compiler (such as the compiler 1040), assembler, interpreter, or the like, which may or may not be included within the memory 1020, so as to operate properly in connection with the O/S 1050. Furthermore, the application 1060 can be written as (a) an object oriented programming language, which has classes of data and methods, or (b) a procedure programming language, which has routines, subroutines, and/or functions.

The I/O devices 1070 may include input devices (or peripherals) such as, for example but not limited to, a mouse, keyboard, scanner, microphone, camera, etc. Furthermore, the I/O devices 1070 may also include output devices (or peripherals), for example but not limited to, a printer, display, etc. Finally, the I/O devices 1070 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 1070 also include components for communicating over various networks, such as the Internet or an intranet. The I/O devices 1070 may be connected to and/or communicate with the processor 1010 utilizing Bluetooth connections and cables (via, e.g., Universal Serial Bus (USB) ports, serial ports, parallel ports, FireWire, HDMI (High-Definition Multimedia Interface), etc.).

When the computer 1000 is in operation, the processor 1010 is configured to execute software stored within the memory 1020, to communicate data to and from the memory 1020, and to generally control operations of the computer 1000 pursuant to the software. The application 1060 and the O/S 1050 are read, in whole or in part, by the processor 1010, perhaps buffered within the processor 1010, and then executed.

When the application 1060 is implemented in software it should be noted that the application 1060 can be stored on virtually any computer readable storage medium for use by or in connection with any computer related system or method. In the context of this document, a computer readable storage medium may be an electronic, magnetic, optical, or other physical device or means that can contain or store a computer program for use by or in connection with a computer related system or method.

The application 1060 can be embodied in any computer-readable medium 1020 for use by or in connection with an instruction execution system, apparatus, server, or device, such as a computer-based system, processor-containing system, or other system that can fetch the instructions from the instruction execution system, apparatus, or device and execute the instructions. In the context of this document, a "computer-readable storage medium" can be any means that can store, read, write, communicate, or transport the program for use by or in connection with the instruction execution system, apparatus, or device. The computer readable medium can be, for example but not limited to, an electronic, magnetic, optical, or semiconductor system, apparatus, or device.

More specific examples (a nonexhaustive list) of the computer-readable medium 1020 would include the following: an electrical connection (electronic) having one or more wires, a portable computer diskette (magnetic or optical), a random access memory (RAM) (electronic), a read-only memory (ROM) (electronic), an erasable programmable read-only memory (EPROM, EEPROM, or Flash memory) (electronic), an optical fiber (optical), and a portable compact disc memory (CDROM, CD R/W) (optical).

In exemplary embodiments, where the application 1060 is implemented in hardware, the application 1060 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It is understood that the computer 1000 includes non-limiting examples of software and hardware components that may be included in various devices, servers, and systems discussed herein, and it is understood that additional software and hardware components may be included in the various devices and systems discussed in exemplary embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or schematic diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As described above, embodiments can be embodied in the form of computer-implemented processes and apparatuses for practicing those processes. In embodiments, the invention is embodied in computer program code executed by one or more network elements. Embodiments include a computer program product on a computer usable medium with computer program code logic containing instructions embodied in tangible media as an article of manufacture. Exemplary articles of manufacture for computer usable medium may include floppy diskettes, CD-ROMs, hard drives, universal serial bus (USB) flash drives, or any other computer-readable storage medium, wherein, when the computer program code logic is loaded into and executed by a computer, the computer becomes an apparatus for practicing the invention. Embodiments include computer program code logic, for example, whether stored in a storage medium, loaded into and/or executed by a computer, or transmitted over some transmission medium, such as over electrical wiring or cabling, through fiber optics, or via electromagnetic radiation, wherein, when the computer program code logic is loaded into and executed by a computer, the computer becomes an apparatus for practicing the invention. When implemented on a general-purpose microprocessor, the computer program code logic segments configure the microprocessor to create specific logic circuits.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for electrically differentiating bases or identifying biomolecules, comprising:
   configuring a reservoir structure separated into a top structure part and a bottom structure part by a membrane; and
   configuring a nanopore formed through the membrane, the nanopore in communication with the top and bottom structure parts of the reservoir structure;
   wherein the membrane comprises a bottom insulation layer, a graphene layer directly on top of the bottom insulation layer, and a top insulation layer directly on top of the graphene layer;
   wherein a first portion of the top insulation layer is directly on top of a first metal pad and a second portion of the top insulation layer is directly on top of a second metal pad;
   wherein the first and second metal pads are formed directly on top of portions of the bottom insulation layer, such that the first metal pad forms a first step on the bottom insulation layer and such that the second metal pad forms a second step on the bottom insulation layer, the first step being under a left top insulation layer and the second step being under a right top insulation layer, the left and right top insulation layers being separate from the top insulation layer;
   wherein the top structure part of the reservoir structure is directly on top of the top insulation layer at a first location above the first portion of the top insulation layer and is directly on top of the top insulation layer at a second location above the second portion of the top insulation layer;
   wherein the graphene layer, in a length direction of the graphene layer, is formed with a left graphene part and a right graphene part connected by a middle graphene part, the middle graphene part of the graphene layer having a smaller width, in a width direction of the graphene layer, than a wider width of the left graphene part and the right graphene part;
   wherein the nanopore is formed through a center of the middle graphene part of the graphene layer, through a lower portion of the top insulation layer, and through the bottom insulation layer, such that a circumference of the nanopore is encompassed entirely in the center of the middle graphene part;
   wherein a hole is formed through an upper portion of the top insulation layer while the nanopore is formed through the lower portion, the hole being larger than the nanopore;
   wherein the graphene layer is wired to first and second metal pads to form a graphene transistor in which transistor current flowing through the graphene transistor is modulated by charges or dipoles passing through the nanopore, the charges or dipoles corresponding to at least one of a nucleobase and a biomolecule; and
   wherein the nanopore is coated with an organic layer formed on the lower portion of the top insulation layer, the graphene layer, and the bottom insulation layer, the organic layer configured to at least one of interact with the nucleobase differently than other nucleobases and interact with the biomolecule differently than other biomolecules.

2. The method of claim 1, wherein when the charges or dipoles correspond to the nucleobase of a nucleic acid molecule and when the nucleobase is in the nanopore, the transistor current modulates based on the charges or dipoles of the nucleobase to form a transistor current pulse.

3. The method of claim 2, wherein the nucleobase is determined based on at least one of a magnitude, a time duration, and a shape of the transistor current pulse when the nucleobase is in the nanopore.

4. The method of claim 1, wherein when the charges or dipoles correspond to the biomolecule and when the biomolecule is in the nanopore, the transistor current modulates based on the charges or dipoles of the biomolecule to form a transistor current pulse.

5. The method of claim 4, wherein the biomolecule is determined based on at least one of a magnitude, a time duration, and a shape of the transistor current pulse when the biomolecule is in the nanopore.

6. The method of claim 1, wherein when a voltage is applied across the nanopore, an ionic current is changed based on a size of the biomolecule to form an ionic current pulse;

wherein the biomolecule is determined based on a magnitude and a time duration of the ionic current pulse when the biomolecule is in the nanopore.

* * * * *